United States Patent
Yamashita et al.

(10) Patent No.: US 6,784,314 B2
(45) Date of Patent: Aug. 31, 2004

(54) PROCESS FOR PRODUCING AMINE DERIVATIVES

(75) Inventors: Makoto Yamashita, Amagasaki (JP);
Kaneyoshi Kato, Kawanishi (JP);
Hiroyuki Tawada, Takatsuki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/240,574

(22) PCT Filed: Apr. 2, 2001

(86) PCT No.: PCT/JP01/02845

§ 371 (c)(1),
(2), (4) Date: Oct. 1, 2002

(87) PCT Pub. No.: WO01/74756

PCT Pub. Date: Oct. 11, 2001

(65) Prior Publication Data

US 2003/0139602 A1 Jul. 24, 2003

(30) Foreign Application Priority Data

Apr. 3, 2000 (JP) ........................................ 2000-105398

(51) Int. Cl.[7] ............................................ C07C 233/05
(52) U.S. Cl. ..................... 564/172; 546/205; 548/530
(58) Field of Search ..................... 564/172; 546/205; 548/530

(56) References Cited

U.S. PATENT DOCUMENTS

| 5,137,901 A | 8/1992 | Junge et al. |
| 6,048,877 A | 4/2000 | Ahmad et al. |
| 6,310,107 B1 | 10/2001 | Kato et al. |

FOREIGN PATENT DOCUMENTS

| AU | A 31189/89 | 9/1989 |
| EP | A0754455 | 1/1997 |
| JP | A 63-77842 | 4/1988 |
| JP | 11-310561 | * 11/1999 |
| WO | WO-A 92/15558 | 9/1992 |
| WO | WO-A 95/32967 | 12/1995 |
| WO | WO 98/06691 | 2/1998 |
| WO | 9838156 | * 9/1998 |

* cited by examiner

*Primary Examiner*—Shailendra Kumar
(74) *Attorney, Agent, or Firm*—Elaine M. Ramesh; Mark Chao

(57) ABSTRACT

This invention provides a convenient and industrially advantageous process producing amine derivatives having the action of inhibiting the secretion and accumulation of amyloid β protein.

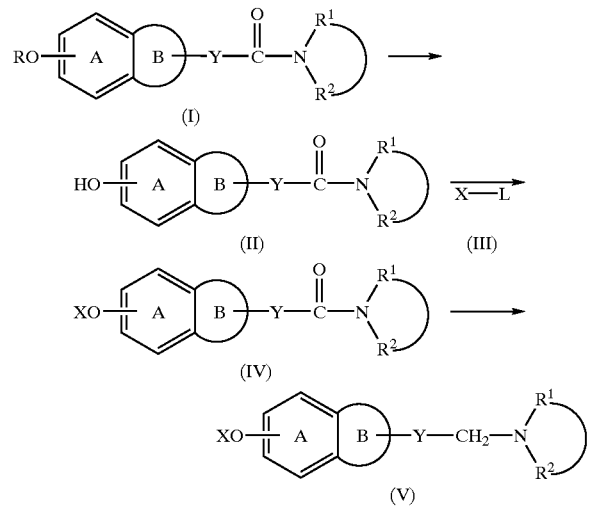

In Compound (I), the ether linkage is selectively cleaved without cleaving the amide linkage present in the same molecule and tertiary amines are not converted into quaternary salts, and thus Amine Derivative (V) with good qualities having the action of inhibiting the secretion and accumulation of amyloid β protein can be obtained in high yield.

10 Claims, 1 Drawing Sheet

PROCESS FOR PRODUCING AMINE DERIVATIVES

This application is the National Phase filing of International Patent Application No. PCT/JP01/02845, filed Apr. 2, 2001.

TECHNICAL FIELD

This invention relates to a convenient process for producing amine derivatives having the action of inhibiting the secretion and accumulation of amyloid β protein and useful as a pharmaceutical preparation, as well as useful synthetic intermediates thereof.

BACKGROUND ART

As amine derivatives having the action of inhibiting the secretion and accumulation of amyloid β protein and a process for producing the amine derivatives, the following process is described in JP-A 11-80098.
[formula]

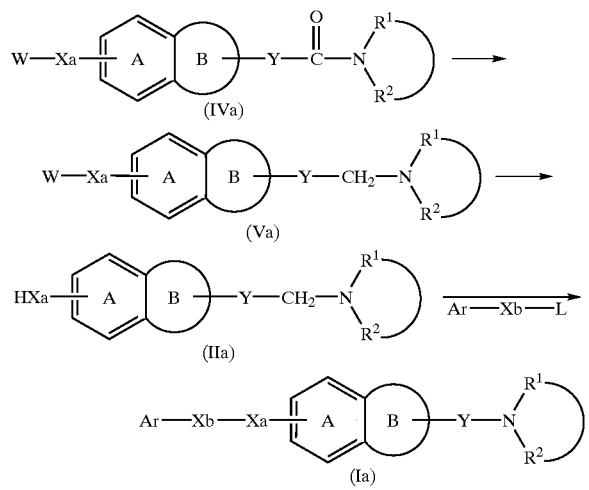

wherein W represents a hydrogen atom or a protective group, Xa represents an oxygen atom etc., Y represents an optionally substituted divalent $C_{1-6}$ aliphatic hydrocarbon group (excluding methylene) which may be bound via an oxygen atom or a sulfur atom, $R^1$ and $R^2$ each represent a hydrogen atom or an optionally substituted lower alkyl, or may, together with their adjacent nitrogen atom, form an optionally substituted nitrogen-containing heterocyclic ring, ring A represents a benzene ring which may further have a substituent group, ring B represents a 4- to 8-membered ring which may further have a substituent group, Ar represents an optionally substituted ring-assembled aromatic group or an optionally substituted condensed aromatic group, Xb represents a bond etc., and L represents an leaving group or hydroxy.

In the process described above, the amide moiety of Compound (IVa) is reduced to give Compound (Va), and then the ether linkage is cleaved to give Compound (IIa). This is because, when an amide linkage and an ether linkage are present in the same molecule, selective cleavage of the ether linkage is generally difficult and thus the amide linkage is also simultaneously cleaved.

In the above process, it was revealed that in the step of subjecting Compound (IIa) to alkylation reaction to form Compound (Ia), the tertiary amine is also alkylated to form a quaternary amine salt, thus causing a reduction in the yield of the desired amine derivative.

There is demand for development of a convenient and industrially advantageous process for producing an amine derivative having the action of inhibiting the secretion and accumulation of amyloid β protein.

SUMMARY OF INVENTION

Figure 1:
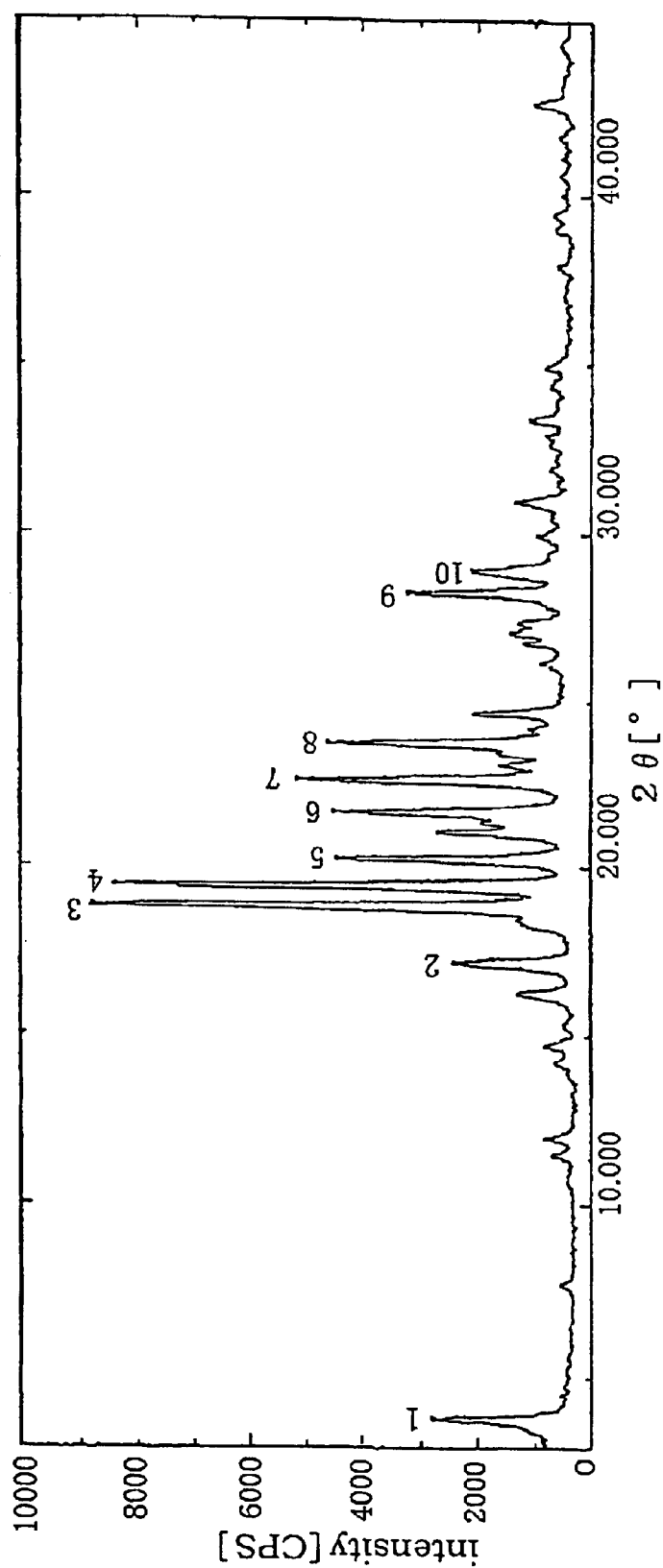
FIG. 1 shows a powdery X-ray crystal diffraction pattern of crystals obtained in Example 1.

As a result of extensive study, the present inventor found that a compound represented by the formula:

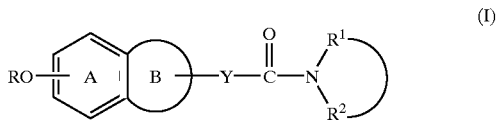

(I)

wherein R represents an optionally substituted hydrocarbon group, $R^1$ and $R^2$ each represent a hydrogen atom or an optionally substituted $C_{1-6}$ alkyl group, or may, together with their adjacent nitrogen atom, form an optionally substituted nitrogen-containing heterocyclic ring, ring A represents an optionally substituted benzene ring, ring B represents an optionally substituted 4- to 8-membered ring, and Y represents an optionally substituted divalent $C_{1-6}$ aliphatic hydrocarbon group which may have an oxygen atom or a sulfur atom, or a salt thereof is selectively cleaved at the ether linkage thereof, to produce a compound represented by the formula:

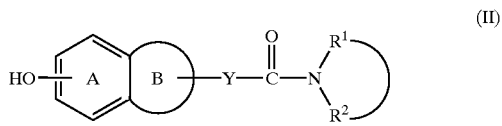

(II)

wherein the symbols have the same meanings as defined above, then this product is reacted with a compound represented by the formula:

X—L  (III)

wherein X represents an optionally substituted hydrocarbon group or an optionally substituted cyclic group, and L represents an leaving group or a hydroxyl group, to produce a compound represented by the formula:

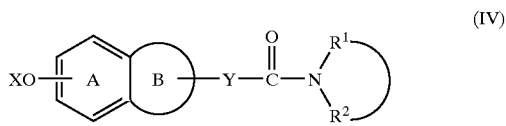

(IV)

wherein the symbols have the same meanings as defined above, and then this compound is subjected to reduction reaction, whereby the desired compound represented by the formula:

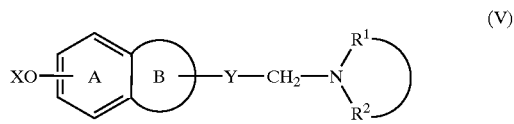

(V)

wherein the symbols have the same meanings as defined above, or a salt thereof can be produced in high yield and high qualities without converting the tertiary amine into a quaternary amine salt, and on the basis of this finding, this invention was completed.

That is, the present invention provides:

(1) A process for producing a compound represented by the formula:

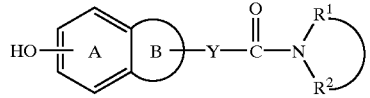

wherein $R^1$ and $R^2$ each represent a hydrogen atom or an optionally substituted $C_{1-6}$ alkyl group, or may, together with their adjacent nitrogen atom, form an optionally substituted nitrogen-containing heterocyclic ring, ring A represents an optionally substituted benzene ring, ring B represents an optionally substituted 4- to 8-membered ring, and Y represents an optionally substituted divalent $C_{1-6}$ aliphatic hydrocarbon group, or a salt thereof, comprising selectively cleaving the ether linkage of a compound represented by the formula:

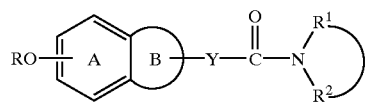

wherein R represents an optionally substituted hydrocarbon group and the other symbols have the same meanings as defined above, or a salt thereof;

(2) The process according to above-mentioned (1), wherein the ether linkage is selectively cleaved in the presence of an acid and mercaptan or sulfide;

(3) The process according to above-mentioned (2), wherein the acid is Lewis acid;

(4) The process according to above-mentioned (2), wherein the acid is sulfonic acid;

(5) The process according to above-mentioned (1), wherein the ether linkage is selectively cleaved in the presence of methanesulfonic acid and methionine;

(6) The process according to above-mentioned (1), wherein R is an optionally substituted $C_{1-6}$ alkyl or optionally substituted $C_{7-19}$ aralkyl group;

(7) The process according to above-mentioned (1), wherein the ether linkage of (+)-N,N-dimethyl-(6-methoxy-2-tetralin)acetamide is selectively cleaved, to produce (+)-N,N-dimethyl-(6-hydroxy-2-tetralin)acetamide;

(8) A process for producing a compound represented by the formula:

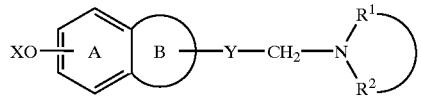

wherein $R^1$ and $R^2$ each represent a hydrogen atom or an optionally substituted $C_{1-6}$ alkyl group, or may, together with their adjacent nitrogen atom, form an optionally substituted nitrogen-containing heterocyclic ring, ring A represents an optionally substituted benzene ring, ring B represents an optionally substituted 4- to 8-membered ring, X represents an optionally substituted hydrocarbon group or an optionally substituted cyclic group, and Y represents an optionally substituted divalent $C_{1-6}$ aliphatic hydrocarbon group, or a salt thereof, comprising selectively cleaving the ether linkage of a compound represented by the formula:

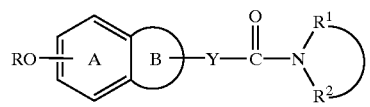

wherein R represents an optionally substituted hydrocarbon group and the other symbols have the same meanings as defined above, or a salt thereof, to produce a compound represented by the formula:

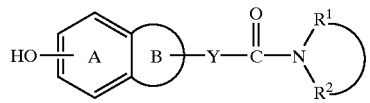

wherein the symbols have the same meanings as defined above, or a salt thereof, then reacting the same with a compound represented by the formula:

$$X-L$$

wherein X has the same meaning as defined above and L represents a leaving group or a hydroxyl group, to produce a compound represented by the formula:

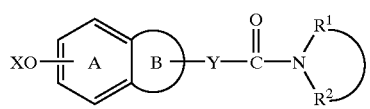

wherein the symbols have the same meanings as defined above, or a salt thereof, and then subjecting the same to reduction reaction;

(9) The process according to above-mentioned (8), wherein X is an optionally substituted ring-assembled aromatic group or an optionally substituted condensed aromatic group;

(10) The process according to above-mentioned (8), which comprises selectively cleaving the ether linkage of (+)-N,N-dimethyl-(6-methoxy-2-tetralin)acetamide, to produce (+)-N,N-dimethyl-(6-hydroxy-2-tetralin)acetamide, then reacting the same with 4-chloromethylbiphenyl to produce (+)-N,N-dimethyl-(6-(4-biphenylyl)methoxy-2-tetralin)acetamide, and then subjecting the same to reduction reaction, to produce (R)-(+)-6-(4-biphenylyl)methoxy-2-[2-(N,N-dimethylamino)ethyl]tetralin hydrochloride monohydrate;

(11) A compound represented by the formula:

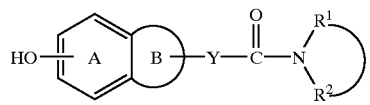

wherein $R^1$ and $R^2$ each represent a hydrogen atom or an optionally substituted $C_{1-6}$ alkyl group, or may, together with their adjacent nitrogen atom, form an optionally substituted nitrogen-containing heterocyclic ring, ring A represents an optionally substituted benzene ring, ring B represents an optionally substituted 4- to 8-membered ring, and Y represents an optionally substituted divalent $C_{1-6}$ aliphatic hydrocarbon group, or a salt thereof;

(12) The compound according to above-mentioned (11), which is (+)-N,N-dimethyl-(6-hydroxy-2-tetralin)acetamide;

(13) A compound represented by the formula:

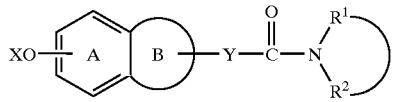

wherein $R^1$ and $R^2$ each represent a hydrogen atom or an optionally substituted $C_{1-6}$ alkyl group, or may, together with their adjacent nitrogen atom, form an optionally substituted nitrogen-containing heterocyclic ring, ring A represents an optionally substituted benzene ring, ring B represents an optionally substituted 4- to 8-membered ring, Y represents an optionally substituted divalent $C_{1-6}$ aliphatic hydrocarbon group, and X represents an optionally substituted hydrocarbon group or an optionally substituted cyclic group, or a salt thereof;

(14) The compound according to above-mentioned (13), which is (+)-N,N-dimethyl-(6-(4-biphenylyl)methoxy-2-tetralin)acetamide;

(15) A process for producing a compound represented by the formula:

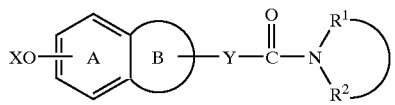

wherein $R^1$ and $R^2$ each represent a hydrogen atom or an optionally substituted $C_{1-6}$ alkyl group, or may, together with their adjacent nitrogen atom, form an optionally substituted nitrogen-containing heterocyclic ring, ring A represents an optionally substituted benzene ring, ring B represents an optionally substituted 4- to 8-membered ring, X represents an optionally substituted hydrocarbon group or an optionally substituted cyclic group, and Y represents an optionally substituted divalent $C_{1-6}$ aliphatic hydrocarbon group, or a salt thereof, comprising allowing a compound represented by the formula:

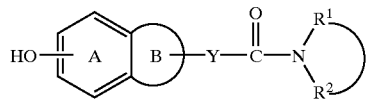

wherein the symbols have the same meanings as defined above, or a salt thereof to react with a compound represented by the formula:

X—L wherein X has the same meaning as defined above and L represents a leaving group or a hydroxyl group;

(16) A process for producing a compound represented by the formula:

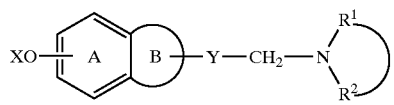

wherein $R^1$ and $R^2$ each represent a hydrogen atom or an optionally substituted $C_{1-6}$ alkyl group, or may, together with their adjacent nitrogen atom, form an optionally substituted nitrogen-containing heterocyclic ring, ring A represents an optionally substituted benzene ring, ring B represents an optionally substituted 4- to 8-membered ring, X represents an optionally substituted hydrocarbon group or an optionally substituted cyclic group, and Y represents an optionally substituted divalent $C_{1-6}$ aliphatic hydrocarbon group, or a salt thereof, comprising allowing a compound represented by the formula:

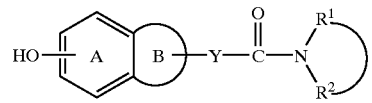

wherein the symbols have the same meanings as defined above, or a salt thereof to react with a compound represented by the formula:

X—L wherein X has the same meaning as defined above and L represents a leaving group or a hydroxyl group, to produce a compound represented by the formula:

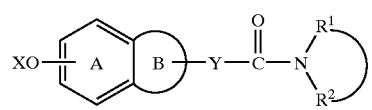

wherein the symbols have the same meanings as defined above, or a salt thereof and then subjecting the same to reduction reaction;

(17) (R)-(+)-6-(4-biphenylyl)methoxy-2-[2-(N,N-dimethylamino)ethyl]tetralin hydrochloride monohydrate;

(18) The compound according to above-mentioned (15), which shows a diffraction pattern having characteristic peaks in spacings (d values) of approximately 23.1, approximately 5.17, approximately 4.72, approximately 4.56, approximately 4.38, approximately 4.10, approximately 3.93, approximately 3.74, approximately 3.16 and approximately 3.09 angstrom by powder X-ray crystal diffraction;

(19) A pharmaceutical composition comprising the compound above-mentioned (17);

(20) The pharmaceutical composition according to above-mentioned (19), which is an agent for preventing or treating Alzheimer's disease;

(21) A method for preventing or treating Alzheimer's disease, which comprises incorporating the compound of above-mentioned (17) into mammals; and

(22) Use of the compound above-mentioned (17) for production of an agent for preventing or treating Alzheimer's disease.

DETAILED DESCRIPTION OF THE INVENTION

In the formula above, the "hydrocarbon group" of the "optionally substituted hydrocarbon group" represented by R includes a $C_{1-6}$ alkyl group (e.g., methyl, ethyl, propyl, isopropyl, butyl, isobutyl, sec-butyl, tert-butyl, pentyl, isopentyl, neopentyl, tert-pentyl, hexyl, isohexyl etc.), $C_{2-6}$ alkenyl group (e.g., vinyl, allyl, isopropenyl, 2-butenyl etc.), $C_{2-6}$ alkynyl group (e.g., ethynyl, propargyl, 2-butynyl etc.), $C_{3-6}$ cycloalkyl group (e.g., cyclopropyl, cyclobutyl, cyclopentyl, cyclohexyl etc.), $C_{6-14}$ aryl group (e.g., phenyl, 1-naphthyl, 2-naphthyl, 2-indenyl, 2-anthryl etc.) and $C_{7-19}$ aralkyl group (e.g., benzyl, phenethyl, diphenylmethyl, triphenylmethyl, 1-naphthylmethyl, 2-naphthylmethyl, 2,2dipbenylethyl, 3-phenylpropyl, 4-phenylbutyl, 5-phenylpentyl etc.).

In the "optionally substituted hydrocarbon group" represented by R, the "substituent group" includes a halogen atom (e.g., fluorine, chlorine, bromine, iodine etc.), $C_{1-3}$ alkylene dioxy (e.g., methylene dioxy, ethylene dioxy etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkyl thio, hydroxy, amino, mono-$C_{1-6}$ alkyl amino (e.g., methylamino, ethylamino, propylamino, isopropylamino, butylamino etc.), di-$C_{1-6}$ alkyl amino (e.g., dimethylamino, diethylamino, dipropylamino, dibutylamino, ethylmethylamino etc.), 5- to 7-membered saturated cyclic amino, formyl, carboxy, carbamoyl, $C_{1-6}$ alkyl-carbonyl (e.g., acetyl, propionyl etc.), $C_{1-6}$ alkoxy-carbonyl (e.g., methoxycarbonyl, ethoxycarbonyl, propoxycarbonyl, tert-butoxycarbonyl etc.), $C_{1-10}$ aryl-carbonyl (e.g., benzoyl, 1-naphthoyl, 2-naphthoyl etc.), $C_{6-10}$ aryloxy-carbonyl (e.g., phenoxycarbonyl etc.), $C_{7-16}$ aralkyloxy-carbonyl (e.g., benzyloxycarbonyl, phenethyloxcarbonyl etc.), 5- to 6-membered heterocyclic carbonyl (e.g., nicotinoyl, isonicotinoyl, 2-thenoyl, 3-thenoyl, 2-furoyl, 3-furoyl, morpholinocarbonyl, piperidinocarbonyl, 1-pyrrolidinylcarbonyl etc.), mono-$C_{1-6}$ alkyl-carbamoyl (e.g., methylcarbamoyl, ethylcarbamoyl etc.), di-$C_{1-6}$ alkyl-carbamoyl (e.g., dimethylcarbamoyl, diethylcarbamoyl, ethylmethylcarbamoyl etc.), $C_{6-10}$ aryl-carbamoyl (e.g., phenylcarbamoyl, 1-naphthylcarbamoyl, 2-naphthylcarbamoyl etc.), 5- to 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbarnoyl etc.), $C_{1-6}$ alkyl sulfonyl (e.g., methylsulfonyl, ethylsulfonyl etc.), $C_{6-10}$ aryl sulfonyl (e.g., benzenesulfonyl, 1-naphthalenesulfonyl, 2-naphthalenesulfonyl etc.), formyl amino, $C_{1-6}$ alkyl-carboxamide (e.g., acetaride etc.), $C_{6-10}$ aryl-carboxamide (e.g., phenylcarboxamide, naphthylcarboxamide etc.), $C_{1-6}$ alkoxy-carboxamide (e.g., methoxycarboxamide, ethoxycarboxamide, propoxycarboxamide, butoxycarboxamide etc.), $C_{1-6}$ alkyl sulfonylamino (e.g., methylsulfonylamino, ethylsulfonylamino etc.), $C_{1-6}$ alkyl-carbonyloxy (e.g., acetoxy, propanoyloxy etc.), $C_{6-10}$ aryl-carbonyloxy (e.g., benzoyloxy, 1-naphthoyloxy, 2-naphthoyloxy etc.), $C_{1-6}$ alkoxy-carbonyloxy (e.g., methoxycarbonyloxy, ethoxycarbonyloxy, propoxycarbonyloxy, butoxycarbonyloxy etc.), mono-$C_{1-6}$ alkyl-carbamoyloxy (e.g., methylcarbamoyloxy, ethylcarbamoyloxy etc.), di-$C_{1-6}$ alkyl-carbamoyloxy (e.g., dimethylcarbamoyl, diethylcarbamoyloxy etc.), $C_{6-10}$ aryl-carbamoyloxy (e.g., phenylcarbamoyloxy, naphthylcarbamoyloxy etc.), nicotinoyloxy and $C_{6-10}$ aryloxy (e.g., phenyloxy, naphthyloxy etc.), and the number of substituent groups is 1 to 5, preferably 1 to 3.

The "optionally halogenated $C_{1-6}$ alkyl" described above includes, for example, $C_{1-6}$ alkyl (e.g., methyl, ethyl, propyl, isopropyl, butyl, isobutyl, sec-butyl, tert-butyl, pentyl, hexyl etc.) which may have 1 to 5, preferably 1 to 3 halogen atoms (e.g., fluorine, chlorine, bromine, iodine etc.). Examples thereof include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl etc.

The "optionally halogenated $C_{3-6}$ cycloalkyl" described above includes, for example, $C_{3-6}$ cycloalkyl (e.g., cyclopropyl, cyclobutyl, cyclopentyl, cyclohexyl etc.) which may have 1 to 5, preferably 1 to 3 halogen atoms (e.g., fluorine, chlorine, bromine, iodine etc.). Examples thereof include cyclopropyl, cyclobutyl, cyclopentyl, cyclohexyl, 4,4-dichlorocyclohexyl, 2,2,3,3-tetrafluorocyclopentyl, 4-chlorocyclohexyl etc.

The "optionally halogenated $C_{1-6}$ alkoxy" described above includes, for example, $C_{1-6}$ alkoxy (e.g., methoxy, ethoxy, propoxy, butoxy, pentyloxy etc.) which may have 1 to 5, preferably 1 to 3 halogen atoms (e.g., fluorine, chlorine, bromine, iodine etc.). Examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy etc.

The "optionally halogenated $C_{1-6}$ alkyl thio" described above includes, for example, $C_{1-6}$ alkyl thio (e.g., methylthio, ethylthio, propylthio, isopropylthio, butylthio, sec-butylthio, tert-butylthio etc.) which may have 1 to 5, preferably 1 to 3 halogen atoms (e.g., fluorine, chlorine, bromine, iodine etc.). Examples thereof include methylthio, difluoromethylthio, trifluoromethylthio, ethylthio, propylthio, isopropylthio, butylthio, 4,4,4-trifluorobutylthio, pentylthio, hexylthio etc.

The "5- to 7-membered saturated cyclic amino" described above includes, for example, morpholino, thiomorpholino, piperazine-1-yl, 4-substituted piperazine-1-yl, piperidino, pyrrolidine-1-yl, hexamethylene-1-yl etc.

The "substituent group" of the "4-substituted piperazine-1-yl", includes, for example, one or two substituent groups selected from $C_{1-6}$ alkyl (e.g., methyl, ethyl- etc.), $C_{6-14}$ aryl (e.g., phenyl etc.), $C_{7-19}$ aralkyl (e.g., benzyl etc.), 5- to 10-membered aromatic heterocyclic group (e.g., 2-, 3- or 4-pyridyl etc.) and acyl (e.g., formyl, acetyl etc.).

R is preferably an optionally substituted $C_{1-6}$ alkyl or optionally substituted $C_{7-19}$ aralkyl group.

In the formula above, the "$C_{1-6}$ alkyl group" of the "optionally substituted $C_{1-6}$ alkyl group" represented by $R^1$ and $R^2$ includes methyl, ethyl, propyl, isopropyl, butyl, isobutyl, sec-butyl, tert-butyl, pentyl, isopentyl, neopentyl, tert-pentyl, hexyl, isohexyl etc.

The "substituent group" and the number thereof for the "optionally substituted $C_{1-6}$ alkyl group" represented by $R^1$ and $R^2$ are exemplified by those for the "optionally substituted hydrocarbon group" represented by R described above.

In the "optionally substituted nitrogen-containing heterocyclic ring" which is formed by $R^1$ and $R^2$ together with their adjacent nitrogen atom, the "nitrogen-containing heterocyclic ring" includes, for example, a 3- to 8-membered nitrogen-containing heterocyclic ring which contains at least one nitrogen atom other than carbon atoms and which may contain 1 to 3 heteroatoms selected from a nitrogen atom, a sulfur atom and an oxygen atom, and examples thereof include aziridine, azetidine, morpholine, thiomorpholine, piperidine, piperazine, pyrrolidine, hexamethyleneimine, heptamethyleneimine, or unsaturated cyclic amines thereof (e.g., 1,2,5,6-tetrahydropyridine etc.). Among these, morpholine, piperidine, piperazine and pyrrolidine are preferred.

The "nitrogen-containing heterocyclic ring" in the "optionally substituted nitrogen-containing heterocyclic ring" may have 1 to 3 substituent groups selected from the "substituent group" in the "optionally substituted hydrocarbon group", oxo and $C_{7-19}$ aralkyl (e.g., benzyl). Preferable substituent groups include, for example, $C_{1-6}$ alkyl (e.g., methyl, ethyl, propyl, isopropyl, butyl etc.), hydroxy, amino, mono-$C_{1-6}$ alkyl amino (e.g., methylamino, ethylamino, propylamino, isopropylamino, butylamino etc.), di-$C_{1-6}$ alkylamino (e.g., dimethylamino, diethylamino, dipropylamino, dibutylamino, ethylmethylamino etc.), 5- to 7-membered saturated cyclic amino (e.g., morpholino, piperazine-1-yl, piperidino, pyrrolidine-1-yl, hexamethyleneimine-1-yl etc.), $C_{1-6}$ alkyl-carboxamide (e.g., acetamide etc.), $C_{1-6}$ alkoxy-carboxamide (e.g., methoxycarboxamide, ethoxycarboxamide etc.), an optionally substituted aromatic group (e.g., $C_{6-10}$ aryl [preferably phenyl, 1- or 2-naphthyl] or a 5- to 6-membered aromatic heterocyclic group [preferably 2-, 3- or 4-pyridyl] which may have 1 to 3 substituent groups selected from a halogen atom, cyano, $C_{1-6}$ alkyl and $C_{1-6}$ alkoxy), oxo, etc.

$R^1$ and $R^2$ are preferably $C_{1-6}$ alkyl such as methyl.

In the formula above, the substituent group of the "optionally substituted benzene ring" represented by the ring A includes, for example, a halogen atom (e.g., fluorine, chlorine, bromine, iodine etc.), optionally halogenated $C_{1-6}$ alkyl (e.g., $C_{1-6}$ alkyl which may have 1 to 5 halogen atoms described above), optionally halogenated $C_{1-6}$ alkoxy (e.g., $C_{1-6}$ alkoxy which may have 1 to 5 halogen atoms described above), hydroxy, amino etc. The ring A may be substituted with one to three of these substituent groups at substitutable positions other than the position of a group represented by the formula —OR, —OH or a group represented by the formula —OX, and when the number of substituent groups is 2 or more, the respective substituent groups may be the same or different.

The ring A is preferably a benzene ring substituted with only a group represented by the above formula —OR, —OH, or a group represented by the above formula —OX.

In the "optionally substituted 4- to 8membered ring" represented by the ring B in the formula above, the "4- to 8-membered ring" includes a 4 to 8-membered homo- or heterocyclic ring which may contain one double bond at a portion other than the portion condensed with the ring A and which may contain 1 to 3 heteroatoms selected from an oxygen atom, a nitrogen atom and a sulfur atom other than carbon atoms. Examples thereof include a ring represented by the formula:

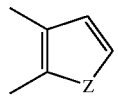

wherein, Z represents (i) a bond, (ii) $C_{1-4}$ alkylene, (iii) $C_{2-4}$ alkenylene, (iv) —O—$CH_2$— (v) —O— $CH_2$—$CH_2$— or (vi) the formula —$NR^8$—$CH_2$— or —$NR^8$—$CH_2$—$CH_2$—, whereupon $R^8$ represents a hydrogen atom, a an optionally substituted hydrocarbon group, or acyl. $R^8$ is preferably a hydrogen atom, optionally halogenated $C_{1-6}$ alkyl (e.g., $C_{1-6}$ alkyl which may have 1 to 5 halogen atoms described above), $C_{1-6}$ alkylcarbonyl (e.g., acetyl, propionyl etc.), $C_{1-6}$ alkoxy-carbonyl (e.g., methoxycarbonyl, ethoxycarbonyl, propoxycarbonyl, tert-butoxycarbonyl etc.), $C_{6-10}$ aryl-carbonyl (e.g., benzoyl, 1-naphthoyl, 2-naphthoyl etc.), $C_{6-10}$ aryloxy-carbonyl (e.g., phenoxycarbonyl etc.), $C_{7-16}$ aralkyloxy-carbonyl (e.g., benzyloxycarbonyl, phenethyloxycarbonyl etc.), 5- to 6-membered heterocyclic carbonyl (e.g., nicotinoyl, isonicotinoyl, 2-thenoyl, 3-thenoyl, 2-furoyl, 3-furoyl, morpholiocarbonyl, piperidinocarbonyl, 1-pyrrolidinylcarbonyl etc.), mono-$C_{1-6}$ alkyl-carbamoyl (e.g., methylcarbamoyl, ethylcarbamoyl etc.), di-$C_{1-6}$ alkyl-carbamoyl (e.g., dimethylcarbamoyl, diethylcarbamoyl, eth-ylmethylcarbamoyl etc.), $C_{6-10}$ aryl-carbamoyl (e.g., phenylcarbamoyl, 1-naphthylcarbamoyl, 2-naphthylcarbamoyl etc.), 5- to 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl etc.), $C_{1-6}$ alkylsulfonyl (e.g., methylsulfonyl, ethylsulfonyl etc.) and $C_{6-10}$ arylsulfonyl (e.g., benzenesulfonyl, 1-naphthalenesulfonyl, 2-naphthalenesulfonyl etc.). $R^8$ is more preferably a hydrogen atom, optionally halogenated $C_{1-6}$ alkyl, $C_{1-6}$ alkylsulfonyl and $C_{1-3}$ alkylsulfonyl.

Z is preferably $C_{1-3}$ alkylene, —$NR^8$—$CH_2$— etc, and more preferably ethylene.

The "4- to 8-membered ring" is preferably a ring represented by the formula:

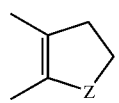

wherein Z has the same meaning as defined above. This ring is preferably a 6-membered homo- or heterocyclic ring which does not contain a double bond in the other portion than the portion condensed with the ring A and which may contain one oxygen atom or imino other than carbon atoms.

In the "optionally substituted 4- to 8-membered ring" represented by the ring B, the "substituent group" includes, for example, oxo, $C_{1-6}$ alkyl (e.g., methyl, ethyl, propyl, isopropyl, butyl etc.), hydroxy etc. The ring B may be substituted with one to three substituent groups at substitutable positions, and when the number of substituent groups is 2 or more, the respective substituent groups may be the same or different.

The ring B is preferably an unsubstituted 6-membered homo- or heterocyclic ring.

The condensed ring formed by the rings A and B is preferably a ring represented by the formula:

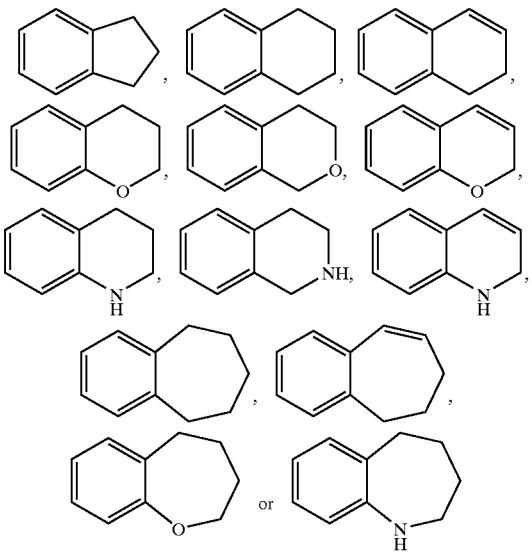

In the "optionally substituted divalent $C_{1-6}$ aliphatic hydrocarbon group" represented by Y in the above formula, the "divalent $C_{1-6}$ aliphatic hydrocarbon group" includes, for example, $C_{1-6}$ alkylene (e.g., methylene, ethylene, propylene etc.), $C_{2-6}$ alkenylene (e.g., vinylene etc.) and $C_{2-6}$ alkynylene (e.g., ethenylene etc.).

The "substituent group" of the "optionally substituted divalent $C_{1-6}$ aliphatic hydrocarbon group" includes, for example, $C_{1-6}$ alkyl (e.g., methyl, ethyl, propyl, isopropyl, butyl, isobutyl, sec-butyl, tert-butyl, pentyl, hexyl etc.). The divalent $C_{1-6}$ aliphatic hydrocarbon group may be substituted with 1 to 3 substituent groups at substitutable positions, and when the number of substituent groups is 2 or more, the respective substituent groups may be the same or different.

Y is preferably a divalent $C_{1-6}$ aliphatic hydrocarbon group, more preferably $C_{1-6}$ alkylene. (e.g., methylene etc.).

The "optionally substituted hydrocarbon group" represented by X in the above formula and the number thereof are exemplified by those for the "optionally substituted hydrocarbon group" represented by R.

The "optionally substituted cyclic group" represented by X is not particularly limited, and may be either an aromatic or non-aromatic cyclic group. Further, this cyclic group may be a homocyclic or heterocyclic ring. The heterocyclic ring is preferably the one containing S, N and/or O as a constituent atom of the ring. Further, the cyclic ring may be either a monocyclic or condensed ring. The number of constituent atoms in one ring is preferably 5 to 8. The "optionally substituted cyclic group" represented by X is particularly preferably an optionally substituted ring-assembled aromatic group or an optionally substituted condensed aromatic group.

The "ring-assembled aromatic group" of the "optionally substituted ring-assembled aromatic group" refers to a group derived by removing an arbitrary hydrogen atom from an aromatic ring cluster wherein two or more (preferably two or three) aromatic rings are directly bound via a single bond and the number of direct bonds to the rings is smaller by one than the number of rings in the cyclic system. The "aromatic ring" includes an aromatic hydrocarbon, an aromatic heterocyclic ring etc.

The "aromatic hydrocarbon" includes, for example, a monocyclic or condensed polycyclic (di- or tricyclic) aromatic hydrocarbon having 6 to 14 carbon atoms (e.g., benzene, naphthalene, indene, anthracene etc.) or quinone having 6 to 14 carbon atoms (e.g., p-benzoquinone, 1,4-naphthoquinone, indane-4,7-dione etc.).

The "aromatic heterocyclic ring" includes, for example, a 5- to 14-membered, preferably 5- to 10-membered aromatic heterocyclic ring containing one or more (e.g., 1 to 4) heteroatoms selected from a nitrogen atom, a sulfur atom and an oxygen atom in addition to the carbon atoms. Specifically, the aromatic heterocyclic ring includes aromatic heterocyclic rings such as thiophene, benzothiophene, benzofuran, benzimidazole, benzoxazole, benzothiazole, benzisothiazole, naphtho[2,3-b]thiophene, furan, phenoxathiine, pyrrole, imidazole, pyrazole, oxadiazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazane, phenoxazine, phthalimide etc., as well as a ring formed by condensing these rings (preferably monocycles) with one or more (preferably one or two) aromatic rings (e.g., benzene ring etc.).

The aromatic ring cluster in which these aromatic rings are bound directly via a single bond includes, for example, an aromatic ring cluster formed from two or three (preferably two) rings selected from a benzene ring, a naphthalene ring and a 5- to 10-membered (preferably 5- or 6-membered) aromatic heterocyclic ring. Examples of the aromatic ring cluster includes biphenyl, 2-phenylnaphthalene, p-terphenyl, o-terphenyl, m-terphenyl, 2-phenylpyridine, 3-phenylpyridine, 4-phenylpyridine, 2-phenylthiophene, 3-phenylthiophene, 2-phenylindole, 3-phenylindole, 5-phenyloxadiazole etc. The aromatic ring cluster is preferably an aromatic ring cluster consisting of 2 or 3 aromatic rings selected from benzene, thiophene, pyridine, pyrimidine, 1,2,4-oxadiazole, 1,3,4-oxadiazole, naphthalene and benzofuran.

Examples of the "ring-assembled aromatic group" include 2-biphenylyl, 3-biphenylyl, 4-biphenylyl, 4-(2-thienyl)phenyl, 4-(3-thienyl)phenyl, 3-(3-pyridyl)phenyl, 4-(3-pyridyl)phenyl, 6-phenyl-3-pyridyl, 5-phenyl-1,3,4-oxadiazole-2-yl, 4-(2-naphthyl)phenyl, 4-(2-benzofuranyl)phenyl etc. Among these, 2-biphenylyl, 3-biphenylyl and 4-biphenylyl are preferred. 4-biphenylyl is particularly preferred.

The "substituent group" and the number thereof for the "optionally substituted ring-assembled aromatic group" are exemplified by those for the "optionally substituted hydrocarbon group" represented by R described above.

For example, the "ring-assembled aromatic group" may have 1 to 5, preferably 1 to 3 of the above substituent groups at substitutable positions in the ring-assembled aromatic group, and when the number of substituent groups is 2 or more, the respective substituent groups may be the same or different.

The "condensed aromatic group" of the "optionally substituted condensed aromatic group" refers to a monovalent group derived by removing an arbitrary hydrogen atom from a condensed polycyclic (preferably di- to tetracyclic, preferably di- or tricyclic) aromatic ring. The "condensed polycyclic aromatic ring" includes a condensed polycyclic aromatic hydrocarbon, a condensed polycyclic aromatic heterocyclic ring etc.

The "condensed polycyclic aromatic hydrocarbon" includes, for example, condensed polycyclic (di- or tricyclic) aromatic hydrocarbons having 10 to 14 carbon atoms (e.g., naphthalene, indene, anthracene etc.)

The "condensed polycyclic aromatic heterocyclic ring" includes, for example, a 9- to 14-membered, preferably 9- to 10-membered condensed polycyclic aromatic heterocyclic ring containing one or more (e.g., one to four) heteroatoms selected from a nitrogen atom, a sulfur atom and an oxygen atom in addition to the carbon atoms. Examples thereof include aromatic heterocyclic rings such as benzofuran, benzimidazole, benzoxazole, benzothiazole, benzisothiazole, naphtho[2,3-b]thiophene, isoquinoline, quinoline, indole, quinoxaline, phenanthridine, phenothiazine, phenoxazine and phthalimide.

Examples of the "condensed aromatic group" include 1-naphthyl, 2-naphthyl, 2-quinolyl, 3-quinolyl, 4-quinolyl, 2-benzofuranyl, 2-benzothiazolyl, 2-benzimidazolyl, 1-indolyl, 2-indolyl, 3-indolyl etc., preferably 1-naphthyl and 2-naphthyl.

The "substituent group" and the number thereof for the "optionally substituted condensed aromatic group" are exemplified by those for the "optionally substituted hydrocarbon group" represented by R above.

X is preferably an optionally substituted ring-assembled aromatic group. The ring-assembled aromatic group is more preferably a group consisting of 2 or 3 aromatic rings selected from benzene, thiophene, pyridine, pyrimidine, 1,2,4-oxadiazole, 1,3,4-oxadiazole, naphthalene and benzofuran, and particularly 2-, 3- or 4-biphenylyl is preferred.

A preferable example of X is a ring-assembled aromatic group which may have one to three substituent groups selected from a halogen atom, $C_{1-3}$ alkylene dioxy, nitro, cyano, optionally halogenated $C_{1-6}$ alkyl, optionally halogenated $C_{1-6}$ alkoxy, optionally halogenated $C_{1-6}$ alkyl thio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocyclic carbonyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl, $C_{6-10}$ arylsulfonyl, formylamino, $C_{1-6}$ alkyl-carboxamide, $C_{6-10}$ aryl-carboxamide, $C_{1-6}$ alkoxy-carboxamide, $C_{1-6}$ alkylsulfonylamino, $C_{1-6}$ alkyl-carbonyloxy, $C_{6-10}$ aryl-carbonyloxy, $C_{16}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{610}$ aryloxy. Among these, more preferable is 2, 3- or 4-biphenylyl (preferably 4-biphenylyl) which may have 1 to 3 substituent groups selected from a halogen atom, $C_{1-3}$ alkylene dioxy, nitro, cyano, optionally halogenated $C_{1-6}$ alkyl, optionally halogenated $C_{1-6}$ alkoxy, optionally halogenated $C_{1-6}$ alkylthio, hydroxy, amino, mono-$C_{1-6}$ alkyl amino, di-$C_{1-6}$ alkyl amino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{1-16}$ aralkyloxy-carbonyl, 5- or 6-membered heterocyclic carbonyl, mono-$C_{1-6}$ alkyl-carbamoyl, di-$C_{1-6}$ alkyl-carbamoyl, $C_{6-10}$ aryl-carbamoyl, 5- or 6-membered heterocyclic carbamoyl, $C_{1-6}$ alkylsulfonyl, $C_{6-10}$ arylsulfonyl, formylamino, $C_{1-6}$ alkyl-carboxamide, $C_{6-10}$ aryl-carboxamide, $C_{1-6}$ alkoxy-carboxamide, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and C6-10 aryloxy.

The "leaving group" represented by L in the formula above includes a halogen atom (e.g., chloro, bromo, iodo etc.), optionally halogenated $C_{1-6}$ alkyl sulfonyloxy (e.g., methanesulfonyloxy, ethanesulfonyloxy, trifluoromethane-sulfonyloxy etc.), and optionally substituted $C_{6-10}$ arylsulfonyloxy. In the "optionally substituted $C_{6-10}$ aryl sulfonyloxy", the substituent group includes 1 to 3 groups selected from a halogen atom, optionally halogenated $C_{1-6}$ alkyl (e.g., $C_{1-6}$ alkyl which may have 1 to 5 halogen atoms described above) and $C_{1-6}$ alkoxy (e.g., $C_{1-6}$ alkoxy which may have 1 to 5 halogen atoms described above). Examples of the "optionally substituted $C_{6-10}$ arylsulfonyloxy" include benzenesulfonyloxy, p-toluenesulfonyloxy, 1-naphthalenesulfonyloxy and 2-naphthalenesulfonyloxy.

L is preferably a halogen atom.

As salts of the compounds represented by the formulae (I), (II), (IV) and (V), for example a salt with an inorganic base, an ammonium salt, a salt with an organic base, a salt with an inorganic acid, a salt with an organic acid, and a salt with a basic or acidic amino acid are used.

Preferable examples of the salt with an inorganic base include, for example, alkali metal salts such as sodium salt, potassium salt etc.; alkaline earth metal salts such as calcium salt, magnesium salt, barium salt etc.; and aluminum salts etc. Preferable examples of the salt with an organic base include, for example, salts with trimethylamine, triethylamine, pyridine, picoline, ethanolamine, diethanolamine, triethanolamine, dicyclohexylamine, N,N'-dibenzylethylenediamine etc. Preferable examples of the salt with an inorganic acid include, for example, salts with hydrochloric acid, hydrobromic acid, nitric acid, sulfuric acid, phosphoric acid, etc. Preferable examples of the salt with an organic acid include, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc. Preferable examples of the salt with a basic amino acid include, for example, salts with arginine, lysine, ornithine etc., and preferable examples of the salt with an acidic amino acid include, for example, salts with aspartic acid, glutamic acid etc.

Among these salts, pharmaceutically acceptable salts are preferred. For example, when acidic functional groups are contained in the compound, inorganic salts such as alkali metal salts (for example, sodium salt, potassium salt etc.), alkaline earth metal salts (for example, calcium salt, magnesium salt, barium salt etc.) or ammonium salts are used, and when basic functional groups are contained in the compound, inorganic salts such as hydrochloride, sulfate, phosphate and hydrobromate or organic salts such as acetate, maleate, fumarate, succinate, methanesulfonate, p-toluenesulfonate, citrate and tartrate are used.

In the process of the present invention, first the ether linkage of the compound represented by the formula (I) or a salt thereof [also referred to hereinafter as Compound (I)] is selectively cleaved to produce Compound (II).

This reaction is carried out usually in the presence of an acid. The acid used in this reaction includes, for example, mineral acids (e.g., hydrochloric acid, hydrobromic acid, sulfuric acid, phosphoric acid etc.), organic acids [e.g., acetic acid, propionic acid, butyric acid, sulfonic acid (e.g., methanesulfonic acid, ethanesulfonic acid, benzenesulfonic acid, toluenesulfonic acid, camphor sulfonic acid) etc.], Lewis acids (e.g., aluminum chloride, tin chloride, iron chloride, titanium chloride, boron trifluoride, boron trichloride etc.). In particular, Lewis acid and sulfonic acid (methanesulfonic acid) are preferred.

Sometimes this reaction may proceed advantageously in the presence of mercaptan or sulfide. Such mercaptan includes, for example, $C_1$ to $C_8$ alkyl mercaptans (e.g., methyl mercaptan, ethyl mercaptan, propyl mercaptan, isopropyl mercaptan, butyl mercaptan, isobutyl mercaptan, pentyl mercaptan, 2-pentyl mercaptan, neopentyl mercaptan, hexyl mercaptan, heptyl mercaptan etc.), dimercaptans (e.g., 1,2-dimercaptoethane, 1,2-mercaptopropane, 1,3-dimercaptopropane, 1,4-mercaptobutane, 1,5-mercaptopentane, 1,6-mercaptohexane etc.), mercaptoacids (e.g., mercaptoacetic acid, 2-mercaptopropionic acid, 3-mercaptopropionic acid, 2-mercaptobutanoic acid etc.), mercaptoamines (e.g., 2-mercaptoethylamine, 3-mercaptopropylamine etc.), amino acids (e.g., cysteine etc.) and aromatic mercaptans (e.g., phenyl mercaptan, naphthyl mercaptan, p-chloromercaptan, mercaptoaniline etc.). The sulfide includes, for example, optionally substituted $C_1$ to $C_8$ alkyl sulfides (e.g., dimethylsulfide, ethylmethylsulfide, diethylsulfide, methylpropylsulfide, butylmethylsulfide, isopropylmethylsulfide, isobutylmethylsulfide, tert-butylmethylsulfide, 2-(methylthio)ethanol, 4-methylthio-1-butanol, ethyl 2-hydroxyethylsulfide, chloromethylmethylsulfide, 2-chloroethylmethylsulfide, ethylenesulfide, propylenesulfide etc.), aromatic sulfides (e.g., diphenylsulfide, benzylphenylsulfide, methyl p-tolylsulfide, thioanisole, 2-bromothioanisole, 4-bromothioanisole, 2-methylthioaniline, 3-methylthioaniline etc.), amino acids (e.g., methionine etc.), disulfides (e.g., dimethyldisulfide, diethyldisulfide, dipropyldisulfide, dibutyldisulfide, diisopropyldisulfide, di-tert-butyldisulfide, ethylmethyldisulfide, methylpropyldisulfide, dicyclohexyldisulfide, benzylmethyldisulfide, benzyldisulfide, allyldisulfide, diphenyldisulfide, p-tolyldisulfide, difurfuryldisulfide, 2,2'-dihydroxy-6,6'-dinaphthyldisulfide, 2-hydroxyethyldisulfide, 3,3-dithiopropionic acid, 4,4'-dithiobutanoic acid, cystine etc.). Among these, mercaptan is preferable, and methionine is also preferably used.

In particular, a combination of methionine and methanesulfonic acid is preferred.

This reaction is carried out usually in a solvent, and any solvents can be used insofar as the reaction is not inhibited, and- such solvents include, for example, halogenated hydrocarbons (e.g., dichloromethane, chloroform, 1,2-dichloroethane, 1,1,2,2-tetrachloroethane etc.), aromatic hydrocarbons (e.g., benzene, toluene, xylene, chlorobenzene, nitrobenzene etc.), ethers (e.g., ethyl ether, isopropyl ether, tetrahydrofuran, dioxane etc.), nitrites (e.g., acetonitrile, propionitrile etc.), esters (methyl acetate, ethyl acetate etc.) and alcohols (e.g., methanol, ethanol, propanol, isopropanol, butanol, methoxy ethanol etc.). These solvents can be used alone or in combination thereof in a suitable ratio. Further, the acid above may also be used as the solvent.

The amount of the acid used is 1 to 200 equivalents, preferably 1 to 50 equivalents, relative to Compound (I).

When the reaction is carried out in the presence of mercaptan, the amount of mercaptan used is 1 to 100 equivalents, preferably 1 to 20 equivalents, relative to Compound (I).

The reaction temperature is usually −30 to 200° C., preferably −10 to 150° C.

The reaction time is usually 0.5 to 24 hours, preferably 1 to 10 hours.

Compound (III) thus obtained can be easily isolated by a means known in the art, for example concentration, transfer to other solvent, solvent extraction, crystallization etc., and the compound of higher purity can be obtained by re-crystallization.

In the process of the present invention, Compound (II) is then reacted with Compound (III) to produce Compound (IV).

This reaction is carried out usually in the presence of a base. As the base, use is made of e.g. tertiary amines (e.g., trimethylamine, triethylamine, tributylamine, N-ethyl diisopropylamine, N-methyl morpholine etc.), aromatic amines (e.g., pyridine, picoline, quinoline, isoquinoline, N,N-dimethyl aniline, N,N-diethyl aniline etc.), alkali metal carbonates (e.g., sodium bicarbonate, potassium carbonate, sodium carbonate, cesium carbonate etc.), alkali metal hydroxides (e.g., potassium hydroxide, sodium hydroxide, calcium hydroxide etc.) and alkali metal alkoxides (e.g., potassium tert-butoxide, sodium methoxide, sodium ethoxide, sodium n-butoxide, sodium tert-butoxide etc.).

This reaction is carried out usually in a solvent, and any solvents can be used insofar as the reaction is not inhibited, and such solvents include, for example, alcohols (e.g., methanol, ethanol, propanol, isopropanol, butanol, methoxyethanol etc.), halogenated hydrocarbons (for example, dichloromethane, chloroform, 1,2-dichloroethane, 1,1,2,2-tetrachloroethane etc.), aromatic hydrocarbons (e.g., benzene, toluene, xylene, chlorobenzene, nitrobenzene, benzotrifluoride etc.), ethers (e.g., ethyl ether, isopropyl ether, tetrahydrofuran, dioxane etc.), nitrites (e.g., acetonitrile, propionitrile etc.), esters (methyl acetate, ethyl acetate etc.), N,N-dimethylformamide, N,N-dimethylacetamide, N-methylpyrrolidone, dimethylsulfoxide etc. These solvents can be used alone or in combination thereof in a suitable ratio.

The amount of Compound (III) used is 1 to 10 equivalents, preferably 1 to 5 equivalents, relative to Compound (II).

The amount of the base used is 1 to 20 equivalents, preferably 1 to 5 equivalents, relative to Compound (I).

The reaction temperature is usually −30 to 200° C., preferably −10 to 150° C.

The reaction time is usually 0.5 to 24 hours, preferably 1 to 10 hours.

Compound (IV) thus obtained can be easily isolated by a means known in the art, for example concentration, transfer to other solvent, solvent extraction, crystallization etc., and the compound of higher purity can be obtained by re-crystallization.

Then, the amide moiety of Compound (IV) is reduced to produce objective Compound (V).

The reducing agent used in this reaction includes, for example, metal hydrides (e.g., aluminum hydride, lithium. aluminum hydride, sodium borohydride, lithium borohydride, lithium cyanoborohydride, sodium dihydro-bis (2-methoxyethoxy)aluminate etc.), borane complexes (e.g., a borane-THF complex, catechol borane etc.), dibutyl aluminum hydride, and a mixture of these metal hydroxides and Lewis acids (e.g., aluminum chloride, titanium tetrachloride, cobalt chloride, boron trifluoride etc.).

This reaction is carried out usually in a solvent. The solvent may be any solvents insofar as the reaction is not inhibited, and use is made of e.g. alcohols (e.g., methanol, ethanol, propanol, isopropanol, butanol, methoxyethanol etc.), halogenated hydrocarbons (e.g., dichloromethane, chloroform, 1,2-dichloroethane, 1,1,2,2-tetrachloroethane etc.), aromatic hydrocarbons (e.g., benzene, toluene, xylene, chlorobenzene, nitrobenzene, benzotrifluoride etc.) and ethers (e.g., ethyl ether, isopropyl ether, tetrahydrofuran, dioxane etc.). Two or more of these solvents may be used in combination in a suitable ratio.

The amount of the reducing agent used is 0.5 to 10 equivalents, preferably 1 to 5 equivalents, relative to Compound (IV).

The reaction temperature is usually −30 to 150° C., preferably −10 to 120° C.

The reaction time is usually 0.5 to 24 hours, preferably 1 to 10 hours.

Compound (V) thus obtained can be easily isolated by a means known in the art, for example concentration, transfer to other solvent, solvent extraction, crystallization etc., and the compound of higher purity can be obtained by re-crystallization.

In the production process described above, Compound (I) used as the starting material can be produced by e.g. the following process.

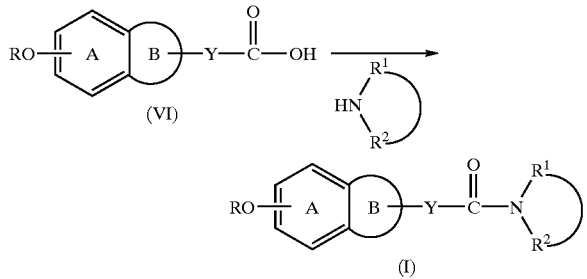

Compound (VI) is subjected to amidation reaction to give Compound (I).

Compound (VI) is an easily available known compound, and examples of the synthesis method include the methods described in JP-A 2-96552, JP-A 6-206851 or Journal of Medicinal Chemistry, page 1326 (1989).

The method of synthesizing (1) 1,2,3,4-tetrahydro-6-methoxynaphthalene-2-acetic acid as a typical example of Compound (VI) wherein R is methyl is described in e.g. Synthetic Communications, 11, 803–809 (1981), and the methods of synthesizing (2) 1,2,3,4-tetrahydro-6-methoxynaphthalene-2-carboxylic acid and 1,2,3,4-tetrahydro-6-methoxynaphthalene-2-butyric acid are described in e.g. Journal of Chemical Society Perkin Transaction I, 1889-1893 (1976).

The "amidation reaction" may be carried out in a method known in the art, for example, (1) Compound (III) is reacted with a compound represented by the formula $HNR^1R^2$ in the present of a dehydration condensing agent, or (2) a reactive derivative of Compound (III) is reacted with a compound represented by the formula $HNR^1R^2$.

In the reaction (1) above, Compound (III), 1 to 5 equivalents of a compound represented by the formula $HNR^1R^2$ and 1 to 2 equivalents of a dehydration condensing agent are reacted in an inert solvent at room temperature for 10 to 24 hours. If necessary, 1 to 1.5 equivalents of 1-hydroxybenzotriazole (HOBT) and (or) 1 to 5 equivalents of a base (e.g., triethylamine etc.) may be added in the reaction mixture.

The "dehydration condensing agent" includes, for example, dicyclohexylcarbodiimide (DCC) and 1-ethyl-3-(3-dimethylaminopropyl)carbodiimide hydrochloride (WSC). In particular, WSC is preferred.

As the inert solvent, for example, nitrile solvents (preferably acetonitrile), amide solvents (preferably DMF), halogenated hydrocarbon solvents (preferably dichloromethane), ether solvents (preferably THF) can be used alone or in combination thereof.

In the reaction (2) above, a reactive derivative of Compound (VI) and 1 to 5 equivalents (preferably 1 to 3 equivalents) of a compound represented by the formula $HNR^1R^2$ are reacted in an inert solvent at −20 to 50° C. (preferably room temperature) for 5 minutes to 40 hours (preferably 1 to 18 hours). The reaction may be carried out if necessary in the coexistence of 1 to 10 equivalents preferably 1 to 3 equivalents of a base.

The "reactive derivative" of Compound (VI) includes acid halides (e.g., acid chloride, acid bromide etc.), a mixed acid anhydrides (e.g., acid anhydrides thereof with $C_{1-6}$ alkyl-carboxylic acid, $C_{6-10}$ aryl-carboxylic acid or $C_{1-6}$ alkyl carbonic acid) and active esters (e.g., esters thereof with optionally substituted phenol, 1-hydroxy benzotriazole or N-hydroxysuccinimide). The "substituent group" of the "optionally substituted phenol" includes one to five groups selected from a halogen atom, nitro, optionally halogenated $C_{1-6}$ alkyl and optionally halogenated $C_{1-6}$ alkoxy. The "optionally substituted phenol" includes, for example, phenol, pentachlorophenol, pentafluorophenol, p-nitrophenol etc. The reactive derivative is preferably an acid halide.

The "base" includes those bases exemplified in the process 1 above, and preferable examples are potassium carbonate, sodium carbonate, sodium hydroxide, potassium hydroxide, sodium bicarbonate, potassium bicarbonate, triethylamine and pyridine.

As the inert solvent, for example an ether solvent, a halogenated hydrocarbon solvent, an aromatic solvent, a nitrile solvent, an amide solvent, a ketone solvent, a sulfoxide solvent, and water can be used alone or as a mixture thereof. In particular, acetonitrile, dichloromethane and chloroform are preferred.

In Compound (V) obtained in the process of the present invention described above, (R)-(+)-6-(4-biphenylyl)methoxy-2-[2- (N,N-dimethylamino)ethyl]tetralin hydrochloride monohydrate [also referred to hereinafter as Compound (V')] is novel, is not denatured even after storage for a long time under usual conditions, and is very excellent in stability. Compound (V') shows a diffraction pattern having characteristic peaks in spacings (d values) of approximately 23.1, approximately 5.17, approximately 4.72, approximately 4.56, approximately 4.38, approximately 4.10, approximately 3.93, approximately 3.74, approximately 3.16 and approximately 3.09 angstrom by powder X-ray crystal diffraction.

Compound (V') has an excellent action of inhibiting the production and secretion of β-amyloid protein, and is thus effective for preventing and treating diseases attributable to β-amyloid protein.

Further, Compound (V') is low toxic and excellent in transfer to the brain.

Accordingly, Compound (V') is useful as a safe agent for preventing and treating diseases attributable to β-amyloid protein, particularly to production and secretion of β-amyloid protein, in mammals (e.g., rats, mice, guinea pigs, rabbits, sheep, horses, pigs, cattle, monkeys, humans etc.).

The diseases include diseases such as, for example, senile dementia, Alzheimer's disease, Down's syndrome and Parkinson's disease, amyloid angiopathy, and disturbance caused by β-amyloid protein at the time of cerebrovascular disturbance, and Compound (V') is particularly preferably used against Alzheimer's disease.

Compound (V') can be formed into a pharmaceutical preparation by means known in the art, and Compound (V') can be safely administered orally or parenterally (for example, through topical, rectal or intravenous administration) as it is or as a pharmaceutical composition in the form of e.g. tablets (including sugar-coated tablets, film-coated tablets), powders, granules, capsules (including soft capsules), solutions, injections, suppositories and sustained release agents prepared by suitably mixing it with a suitable amount of pharmacologically acceptable excipients in the pharmaceutical manufacturing process.

The content of Compound (V') in the pharmaceutical composition is usually about 0.1 to 100% by weight of the whole composition. The dose is varied depending on the subject of administration, administration route, intended diseases etc., and, for example, when used as the agent for treating Alzheimer's disease, the active ingredient (Compound (V')) can be administered orally to an adult (approximately 60kg) in an amount of approximately 0.1 to 500 mg, preferably about 1 to 100 mg, more preferably 5 to 100 mg in one portion, and may be administered in one to several divided portions a day.

The pharmaceutically acceptable carriers used in the production of the pharmaceutical composition include a wide variety of conventional organic or inorganic carrier materials as pharmaceutical materials, for example, excipients, lubricants, binders or disintegrators in solid preparations; solvents, solubilizers, suspension agents, isotonizing agents, buffers and analgesics in liquid preparations. If necessary, additives such as preservatives, antioxidants, coloring agents, sweeteners, adsorbents, wetting agent etc. can also be used.

The excipients used include, for example, lactose, white sugar, D-mannitol, starch, corn starch, microcrystalline cellulose and light silicic anhydride.

The lubricants used include, for example, magnesium stearate, calcium stearate, talc and colloidal silica.

The binders used include, for example, microcrystalline cellulose, white sugar, D-mannitol, dextrin, hydroxypropylcellulose, hydroxypropylmethylcellulose, polyvinyl pyrrolidone, starch, sucrose, gelatin, methylcellulose, sodium carboxymethylcellulose etc.

The disintegrators used include, for example, starch, carboxymethylcellulose, calcium carboxymethylcellulose, sodium croscarmellose, sodium carboxymethyl starch, L-hydroxypropylcellulose etc.

The solvents used include, for example, injection water, alcohol, propylene glycol, Macrogol, sesame oil, corn oil etc.

The solubilizers used include, for example, polyethylene glycol, propylene glycol, D-mannitol, benzyl benzoate, ethanol, trisaminomethane, cholesterol, triethanolamine, sodium carbonate, sodium citrate etc.

The suspension agents used include, for example, surfactants such as stearyl triethanolamine, sodium laurylsulfate, lauryl aminopropionic acid, lecithin, benzalconium chloride, benzethonium chloride and glycerine monostearate, and hydrophilic polymers such as polyvinyl alcohol, polyvinyl pyrrolidone, sodium carboxymethylcellulose, methylcellulose, hydroxymethylcellulose, hydroxyethylcellulose and hydroxypropylcellulose.

The isotonizing agents used include, for example, glucose, D-sorbitol, sodium chloride, glycerine, D-mannitol etc.

The buffers used include, for example, buffers such as phosphates, acetates, carbonates and citrates.

The analgesics used include, for example, benzyl alcohol etc.

The preservatives used include, for example, paraoxybenzoates, chlorobutanol, benzyl alcohol, phenethyl alcohol, dehydroacetic acid, and soibic acid.

The antioxidants used include, for example, sulfites, ascorbic acid etc.

Hereinafter, the present invention is described by the following Reference Examples and Examples, which however are not intended to limit the present invention.

REFERENCE EXAMPLE 1

2-(6-Methoxy-1-oxotetralin-2-ylidene)acetic acid 150 g of 6-methoxy-1-tetralone, 1812 g of 40% aqueous glyoxylic acid, 2300 ml diglyme and 638 ml purified water were mixed. 283 ml conc. sulfuric acid was added dropwise thereto under stirring at room temperature, and then the mixture was stirred at 103 to 105° C. for 6 hours. After the reaction solution was cooled with water and stirred for 1 hour, the precipitated crystals were collected by filtration and washed S times with 1.6 L purified water. By drying it under reduced pressure at 50° C., the title compound, 1215 g (yield 80.2%), was obtained as pale brown yellow crystals.

$^1$H-NMR (300 MHz, CDCl$_3$) ppm; 2.98–3.03 (2H, m), 3.41–3.45 (2H, m), 3.89 (3H, s), 6.73 (1H, d), 6.87–91 (2H, m) 8.09 (1H, d).

REFERENCE EXAMPLE 2

2-(6-Methoxy-1-oxotetralin-2-yl)acetic acid 1212 g of 2-(6-methoxy-1-oxotetralin-2-ilydene)acetic acid, 3636 ml acetic acid and 1357 ml purified water were mixed. 409 g zinc powder was added by small portions to this suspension, and the mixture was heated under reflux for 2 hours, and when the solution was hot, the zinc was removed by filtration. The vessel and the zinc were washed with 606 ml acetic acid of 80° C., and 2885 ml hot water was added dropwise to the filtrate which was then cooled with water and stirred for 1 hour. The precipitated crystals were collected by filtration and washed 4 times with 1.45 L purified water. By drying it under reduced pressure at 50° C., the title compound, 1173 g (yield 95.9%), was obtained as brown yellow crystals.

$^1$H-NMR (300 MHz, DMSO) ppm; 1.92 (1H, m), 2.12 (1H, m), 2.38 (1H, m), 2.72 (1H, m), 2.84–3.06 (3H, m), 3.84 (3H, s), 6.90 (2H, m), 7.84 (1H, m).

REFERENCE EXAMPLE 3

N,N-dimethyl-(6-methoxy-1-oxo-2-tetralin) acetamide 1170 g of 2-(6-methoxy-1-oxotetralone-2-yl)acetic acid, 7020 ml acetonitrile and 733 ml triethylamine were mixed. 645 ml pivaloyl chloride was added dropwise thereto at 5 to 10° C. under a nitrogen atmosphere and stirred at the same temperature for 1 hour, then 611 g dimethylamine hydrochloride was added thereto, 1047 ml triethylamine was added dropwise thereto at 1 to 10° C., and the mixture was stirred at room temperature. 3510 ml purified water was added to the reaction solution, which was then extracted with 14.04 L ethyl acetate, and the organic layer was washed twice with 3510 ml of 5% sodium bicarbonate and then with 3510 ml purified water. The organic layer was concentrated under reduced pressure such that the amount of the remaining solution became 3510 g. The remaining solution was crystallized by adding 2750 ml diusopropyl ether, and 6030 ml diisopropyl ether was added dropwise thereto and stirred for 1 hour under cooling on ice. The precipitated crystals were collected by filtration, washed twice with 2.20 L diisopropyl ether and dried under reduced pressure at 50° C. to give 1061 g of the title compound (yield 81.3%) as brown yellow crystals.

$^1$H-NMR (300 MHz, CDCl$_3$) ppm; 1.91 (1H, m), 2.26–3.34 (2H, m), 2.93 (1H, m), 2.99 (3H, s), 3.08 (3H, s), 3.10–3.21 (3H, m), 3.85 (3H, s), 6.68 (1H, d), 6.81 (1H, m), 7.99 (1H, d).

REFERENCE EXAMPLE 4

N,N-dimethyl-(1-hydroxy-6-methoxy-2-tetralin) acetamide 1056 g of N,N-dimethyl-(6-methoxy-1-oxo-2-tetralin) acetamide and 5280 ml methanol were mixed, and a solution of 198.8 g sodium tetrahydroborate in 1190 ml dimethylacetamide was added dropwise thereto at 5 to 20° C. under a N$_2$ atmosphere, heated and stirred at an internal temperature of 33 to 35° C. for 2.5 hours. The reaction solution was cooled and neutralized at 5 to 10° C. by dropping hydrochloricacid, then 5280 ml purified water was added, the reaction solution was concentrated under reduced pressure until its volume was reduced by about half, 5280 ml purified water was added to the remaining solution which was then concentrated again under reduced pressure such that the amount of the remaining solution became 5280 g. The precipitated crystals were collected by filtration, washed with 2020 ml cold water and dried at 40° C. under reduced pressure, to give 870.8 g of the title compound as pale yellow crystals (yield 81.8%).

$^1$H-NMR (300 MHz, CDCl$_3$) ppm; 1.56–1.63 (1H, m), 1.93–1.97 (1H, m), 2.25–2.28 (1H, m),2.28–2.46 (1H, m), 2.63–2.90 (3H, m), 2.98 (3H, s), 3.04 (3H, s), 3.69 (1H, bs), 3.78 (3H, s) 4.43 (1H, d), 6.58–6.63 (1H, m), 6.74–6.79 (1H, m), 7.48 (1H, d).

REFERENCE EXAMPLE 5

N,N-dimethyl-[6-methoxy-2-(3,4-dihydronaphthalene)]acetamide 866.0 g of N,N-dimethyl-(1-hydroxy-6-methoxy-2-tetralin)acetamide, 4330 ml toluene and 17.3 g of p-toluenesulfonic acid hydrate were mixed and heated for 3 hours under reflux. The reaction solution was cooled to room temperature, then washed twice with 2165 ml of 5% aqueous sodium bicarbonate and then with 2165 ml purified water, and the organic layer was concentrated under reduced pressure to give 764.7 g of the title compound (yield 94.8%).

$^1$H-NMR (300 MHz, CDCl$_3$) ppm; 2.30 (2H, t), 2.82 (2H, t) 2.98 (3H, s), 3.04 (3H, s), 3.25 (2H, s), 3.79 (3H, s), 6.21 (1H, s), 6.65–6.68 (2H, m), 6.92 (1H, m).

REFERENCE EXAMPLE 6

(+)-N,N-dimethyl-(6-methoxy-2-tetralin)acetamide 0.338 g of bis[[(S)-[2,2'-bis(diphenylphosphino)-1,1'-binaphthyl]]dichlororuthenium]triethylamine was introduced into a 1-L autoclave which was then substituted with argon, and a solution of 190 g N,N-dimethyl-[6-methoxy-2-(3,4-dihydronaphthalene)]acetamide in 570 mL ethanol was injected into the 1-L autoclave under argon pressure. Under hydrogen pressure kept at 5 MPa to 4 MPa, the mixture was reacted at 70° C. for 20 hours. The reaction solution was cooled to 30° C. and removed from the 1-L autoclave, followed by distilling the solvent away under reduced pressure, to give 285 g product. 630 mL diisopropyl ether was added thereto and subjected to azeotropic distillation until the amount of the remaining solution became 305 g. Then, 550 mL isopropyl ether was added to the remaining solution, the mixture was dissolved by heating at 60° C., 9.5 g active carbon was added thereto and stirred at 60° C. for 15 minutes, the active carbon was separated by filtration, and the filtrate was stirred at room temperature. The precipitated crystals were collected by filtration, washed with 190 mL diisopropyl ether and dried at 40° C. under reduced pressure, to give 163 g of the title compound as white crystals (yield 85%).

$^1$H-NMR (300 MHz, CDCl$_3$) ppm; 1.34–1.48 (m, 1H), 1.95–2.01 (m, 1H), 2.29–2.46 (m, 4H), 2.79–2.91 (m, 3H), 2.97 (s, 3H), 3.02 (s, 3H), 3.76 (s, 3H), 6.61–6.69 (m, 2H), 6.96 (d, 1H, J=8.3Hz).

EXAMPLE 1

(+)-N,N-dimethyl-(6-hydroxy-2-tetralin)acetamide

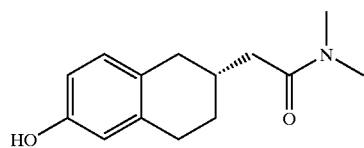

362.8 g of DL-methionine and 546.0 g of (+)-N,N-dimethyl-(6-methoxy-2-tetralin)acetamide were added by small portions to 1638 mL methanesulfonic acid and dissolved. The solution was reacted for 8 hours under heating at an internal temperature of 110° C. under a nitrogen atmosphere. The reaction solution was cooled to an internal temperature of 10° C., and 2730 mL methanol, 1092 mL cold water and 25% cold ammonium hydroxide were added thereto in this order to adjust its pH value to 7.0. After the reaction mixture was stirred at 30° C. for 1 hour, the precipitated crystals were collected by filtration and washed twice with 1640 mL mixture of methanol and tap water (1:2). When the crystals were dried at 50° C. until their weight became constant, the title compound, 475.3 g (yield 87.7%), was obtained as pale yellow crystals.

$^1$H-NMR (300 MHz, DMSO-d$_6$) δ: 1.32–1.36 (1H, m), 1.82–1.86 (1H, m), 2.04–2.08 (1H, m), 2.22–2.32 (3H, m), 2.63–2.74 (3H, m), 2.83 (3H, s), 2.96 (3H, s, 6.45–6.50 (2H, s), 6.79 (1H, d, J=8.1 Hz), 8.96 (1H, s).

EXAMPLE 2

(+)-N,N-dimethyl-(6-(4-biphenylyl)methoxy-2-tetralin)acetamide

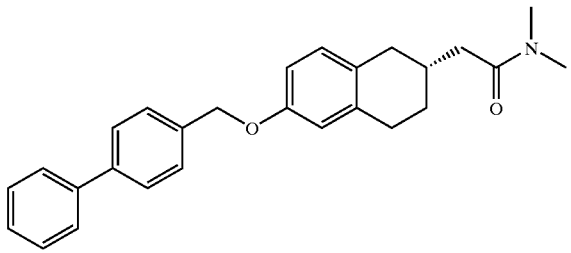

378.6 g of 4-hydroxymethyl biphenyl was dissolved in 1133 ml DMF, and 177.6 mL thionyl chloride was added dropwise thereto at an internal temperature of 20° C. or less. The mixture was reacted at room temperature for 1.5 hours. 2267 mL ethyl acetate was added to the reaction solution and cooled at 10° C., and 1133 mL tap water was added dropwise at 20° C. or less. The organic layer was separated and washed with 1133 mL of 10% aqueous sodium carbonate, 1133 mL of 5% aqueous sodium bicarbonate and 1133 mL water in this order. The organic layer was separated and concentrated under reduced pressure until the amount of the remaining solution became 763 g, then 872 mL DMF was added thereto, and the reaction solution was concentrated under reduced pressure to distill the remaining ethyl acetate away, whereby 1286 g solution of 4-chloromethyl biphenyl in DMF (content, 32.1%; yield, 99.1%) was obtained. 435.9 g (+)-N,N-dimethyl-(6-hydroxy-2-tetralin)acetamide, 516.4 g potassium carbonate and 436 mL DMF were added thereto and stirred for 3 hours at an internal temperature of 80° C. under a nitrogen atmosphere. 1308 mL methanol was added to the reaction solution, 1744 mL water was added thereto at an internal temperature kept at about 60° C., and the mixture was stirred at 60° C. for 30 minutes. Then, the reaction mixture was stirred at 40° C. for 1 hour, and the precipitated crystals were collected by filtration and washed with 1744 mL methanol and then twice with 2180 mL water previously heated at 40° C. By drying the product at 50° C. under reduced pressure, the title compound, 726.8 g (yield 96.7%), was obtained as pale yellow crystals.

$^1$H-NMR (300 MHz, CDCl$_3$) δ: 1.42–1.48 (1H, m), 1.97–2.04 (1H, m), 2.30–2.47 (4H, m), 2.79–2.91 (3H, m), 2.97 (3H, s) 3.01 (3H, s), 5.06 (2H, s), 6.73–6.78 (2H, m), 6.97 (1H, d, J=8.3Hz), 7.34–7.62 (9H, m).

EXAMPLE 3

(R)-(+)-(6-(4-biphenylyl)methoxy-2-[2-(N,N-dimethylamino)ethyl]tetralin hydrochloride monohydrate

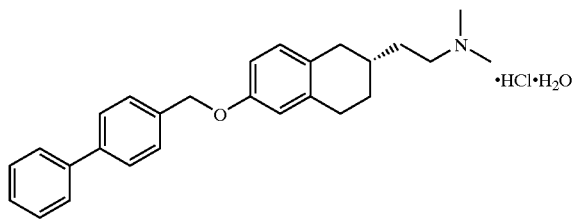

695 g of (+)-N,N-dimethyl-(6-(4-biphenylyl)methoxy-2-tetralin)acetamide was suspended in 3475 mL toluene, and 562 g sodium bis(2-methoxyethoxy)aluminate hydride(70% toluene solution) was added dropwise thereto at an internal temperature of 20° C. or less in a nitrogen atmosphere. The mixture was stirred for 1.5 hours at room temperature, then 695 mL of 4 N aqueous sodium hydroxide was added dropwise at 20° C. or less, the mixture was stirred at room temperature for 30 minutes, and the organic layer was separated. Further, the organic layer was washed twice with 695 mL of 1 N aqueous sodium hydroxide and twice with 1390 mL water. 348 mL toluene was added to the organic layer and heated at 60° C., and 175 mL conc. hydrochloric acid (content: 36%) was added dropwise thereto. The mixture was stirred for 1 hour under cooling on ice, and the precipitated crystals were collected by filtration and washed with 695 mL toluene and 1390 mL of 50% aqueous methanol in this order. By drying the product at 40° C. under reduced pressure, the title compound, 723 g (yield: 94.4%), was obtained as pale yellow crystals. The powder X-ray crystal diffraction pattern is shown in FIG. 1 (measuring device: Rigaku RINT2500V (ultra X18) (Rigaku Denki Co., Ltd.).

| Data on powder x-ray crystal diffraction pattern | |
|---|---|
| Diffraction angle: 2θ (°) | Spacing: d value (angstrom) |
| 3.82 | 23.1 |
| 17.1 | 5.17 |
| 18.8 | 4.72 |
| 19.4 | 4.56 |
| 20.2 | 4.38 |
| 21.7 | 4.10 |
| 22.6 | 3.93 |
| 23.7 | 3.74 |
| 28.2 | 3.16 |
| 28.9 | 3.09 |

$^1$H-NMR (300 MHz, DMSO-$d_6$) δ: 1.32–1.40(1H, m), 1.62–1.74(3H, m), 1.82–1.90(1H, m), 2.28–2.38(1H, m), 2.74(6H, s), 2.76–2.82(3H, br), 3.08–3.16(2H, m), 5.09(2H, s), 6.72–6.80(2H, m), 6.96(1H, d, J=8.0Hz), 7.32–7.38(1H, m), 7.44–7.54(4H, m), 7.64–7.72(4H, m), 10.4(1H, br).

EXAMPLE 4

Purification of (R)-(+)-(6-(4-biphenylyl)methoxy-2-[2-(N,N-dimethylamino)ethyl]tetralin hydrochloride monohydrate 479.8 g of the crude (R)-(+)-(6-(4-biphenylyl)methoxy-2-[2-(N,N-dimethylamino)ethyl]tetralin hydrochloride monohydrate obtained in Example 3 was dissolved in a mixture of 3186 ml tetrahydrofuran and 864 ml water at 60° C. 24 g active carbon was added thereto and stirred at 60° C. for 30 minutes. The active carbon was removed by filtration and washed with a mixture of 336 ml tetrahydrofuran and 216 ml water. The filtrate was heated at 60° C., and 2688 ml tetrahydrofuran was added dropwise thereto under stirring. The reaction solution was cooled to room temperature and stirred at 5 to 10° C. for 2 hours, and the precipitated crystals were collected by centrifugation. The crystals were washed with a mixture of 216 ml tetrahydrofuran and 744 ml water, to give the title compound in a pure form (390.5 g, 85%).

INDUSTRIAL APPLICABILITY

Because the ether linkage is selectively cleaved without cleaving the amide linkage present in the same molecule and tertiary amines are not converted into quaternary salts, the process of the invention is a convenient and industrially advantageous process wherein amine derivatives of high qualities having the action of inhibiting the secretion and accumulation of amyloid β protein can be produced in high yield.

What is claimed is:

1. A process for producing a compound represented by the formula:

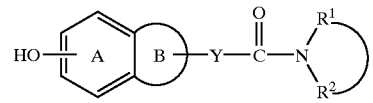

wherein $R^1$ and $R^2$ each represent a hydrogen atom or an optionally substituted $C_{1-6}$ alkyl group, or may, together with their adjacent nitrogen atom, form an optionally substituted nitrogen-containing heterocyclic ring, ring A represents an optionally substituted benzene ring, ring B represents an optionally substituted 4- to 8-membered ring, and Y represents an optionally substituted divalent $C_{1-6}$ aliphatic hydrocarbon group, or a salt thereof, comprising selectively cleaving the ether linkage of a compound represented by the formula:

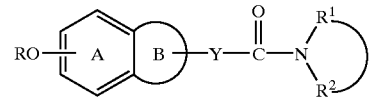

wherein R represents an optionally substituted hydrocarbon group and the other symbols have the same meanings as defined above, or a salt thereof wherein the ether linkage is selectively cleaved in the presence of an acid and mercaptan or sulfide.

2. The process according to claim 1, wherein the acid is Lewis acid.

3. The process according to claim 1, wherein the acid is sulfonic acid.

4. The process according to claim 1, wherein the ether linkage is selectively cleaved in the presence of methanesulfonic acid and methionine.

5. The process according to claim 1, wherein R is an optionally substituted $C_{1-6}$ alkyl or optionally substituted $C_{7-19}$ aralkyl group.

6. The process according to claim 1, wherein the ether linkage of (+)-N,N-dimethyl-(6-methoxy-2-tetralin)acetamide is selectively cleaved, to produce (+)-N,N-dimethyl-(6-hydroxy-2-tetralin)acetamide.

7. A process for producing a compound represented by the formula:

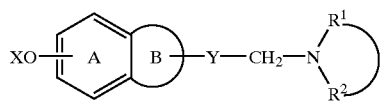

wherein $R^1$ and $R^2$ each represent a hydrogen atom or an optionally substituted $C_{1-6}$ alkyl group, or may, together with their adjacent nitrogen atom, form an optionally substituted nitrogen-containing heterocyclic ring, ring A represents an optionally substituted benzene ring, ring B represents an optionally substituted 4- to 8-membered ring, X represents an optionally substituted hydrocarbon group or an optionally substituted cyclic group, and Y represents an optionally substituted divalent $C_{1-6}$ aliphatic hydrocarbon group, or a salt thereof, comprising selectively cleaving the ether linkage of a compound represented by the formula:

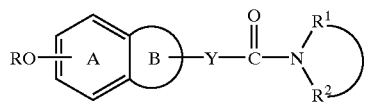

wherein R represents an optionally substituted hydrocarbon group and the other symbols have the same meanings as defined above, or a salt thereof to produce a compound represented by the formula:

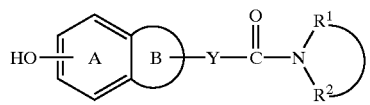

wherein the symbols have the same meanings as defined above, or a salt thereof, then reacting the same with a compound represented by the formula:

wherein X has the same meaning as defined above and L represents an leaving group or a hydroxyl group, to produce a compound represented by the formula

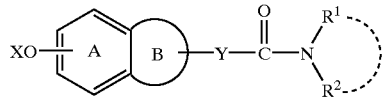

wherein the symbols have the same meanings as defined above, or a salt thereof wherein the ether linkage is selectively cleaved in the presence of an acid and mercaptan or sulfide, and then subjecting the same to reduction reaction.

8. The process according to claim 7, wherein X is an optionally substituted ring-assembled aromatic group or an optionally substituted condensed aromatic group.

9. The process according to claim 7, which comprises selectively cleaving the ether linkage of (+)-N,N-dimethyl-(6methoxy-2-tetralin)acetamide, to produce (+)-N,N-dimethyl-(6-hydroxy-2-tetralin)acetamide, then reacting the same with 4-chloromethylbiphenyl to produce (+)-N,N-dimethyl-(6-(4-biphenylyl)methoxy-2-tetralin)acetamide, and then subjecting the same to reduction reaction, to produce (R)-(+)-6-(4-biphenylyl)methoxy-2-[2-N,N-dimethylamino)ethyl]tetralin hydrochloride monohydrate.

10. A process for producing a compound represented by the formula:

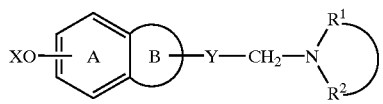

wherein $R^1$ and $R^2$ each represent a hydrogen atom or an optionally substituted $C_{1-6}$ alkyl group, or may, together with their adjacent nitrogen atom, form an optionally substituted nitrogen-containing heterocyclic ring, ring A represents an optionally substituted benzene ring, ring B represents an optionally substituted 4- to 8-membered ring, X represents an optionally substituted hydrocarbon group or an optionally substituted cyclic group, and Y represents an optionally substituted divalent $C_{1-6}$ aliphatic hydrocarbon group, or a salt thereof, comprising allowing a compound represented by the formula:

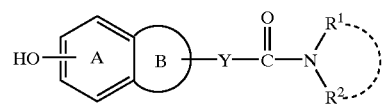

wherein the symbols have the same meanings as defined above, or a salt thereof to react with a compound represented by the formula:

wherein X has the same meaning as defined above and L represents an leaving group or a hydroxyl group, to produce a compound represented by the formula:

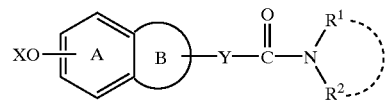

wherein the symbols have the same meanings as defined above, or a salt thereof, and then subjecting the same to reduction reaction.

* * * * *